United States Patent
Gross et al.

(10) Patent No.: US 9,226,683 B2
(45) Date of Patent: Jan. 5, 2016

(54) SYSTEM SCAN TIMING BY ULTRASOUND CONTRAST AGENT STUDY

(75) Inventors: Patrick Gross, Langensendelbach (DE);
Caroline Maleke, Bellevue, WA (US);
Stephen J. Hsu, Issaquah, WA (US);
Chi-Yin Lee, Sammamish, WA (US);
Jerry Hopple, Seattle, WA (US);
Xiaozheng Jenny Zeng, Sammamish, WA (US)

(73) Assignees: Siemens Medical Solutions USA, Inc., Malvern, PA (US); Siemens Aktiengesellschaft (DE)

( * ) Notice: Subject to any disclaimer, the term of this patent is extended or adjusted under 35 U.S.C. 154(b) by 659 days.

(21) Appl. No.: 13/448,319

(22) Filed: Apr. 16, 2012

(65) Prior Publication Data
US 2013/0274589 A1    Oct. 17, 2013

(51) Int. Cl.
| | |
|---|---|
| *A61B 5/055* | (2006.01) |
| *A61B 6/00* | (2006.01) |
| *A61B 8/08* | (2006.01) |
| *G01R 33/48* | (2006.01) |
| *G01R 33/567* | (2006.01) |
| *G01R 33/563* | (2006.01) |

(52) U.S. Cl.
CPC ................ *A61B 5/055* (2013.01); *A61B 6/481* (2013.01); *A61B 6/541* (2013.01); *A61B 8/481* (2013.01); *A61B 8/5223* (2013.01); *G01R 33/4814* (2013.01); *G01R 33/5673* (2013.01); *A61B 8/483* (2013.01); *G01R 33/56366* (2013.01)

(58) Field of Classification Search
USPC .......... 600/410, 411, 425, 427, 437, 439, 458
See application file for complete search history.

(56) References Cited

U.S. PATENT DOCUMENTS

| | | | | |
|---|---|---|---|---|
| 6,315,729 | B1* | 11/2001 | Averkiou et al. | 600/458 |
| 7,606,614 | B2* | 10/2009 | Licato et al. | 600/431 |
| 2005/0031176 | A1 | 2/2005 | Hertel et al. | |
| 2005/0177044 | A1* | 8/2005 | Rubin et al. | 600/437 |
| 2005/0215904 | A1* | 9/2005 | Sumanaweera et al. | 600/458 |
| 2006/0004275 | A1 | 1/2006 | Vija et al. | |
| 2007/0167705 | A1* | 7/2007 | Chiang et al. | 600/411 |
| 2010/0254583 | A1 | 10/2010 | Chan et al. | |
| 2010/0290685 | A1 | 11/2010 | Wein et al. | |
| 2010/0312093 | A1* | 12/2010 | Biglieri et al. | 600/411 |
| 2011/0144495 | A1 | 6/2011 | Wilkening et al. | |

* cited by examiner

Primary Examiner — Peter Luong

(57) ABSTRACT

Scan timing of contrast agent study is provided. Ultrasound is used to determine timing of contrast agent inflow and/or outflow. The timing based on the ultrasound scanning controls scanning for MR or CT imaging. The MR or CT contrast agent imaging for MR or CT contrast agents may be synchronized using the ultrasound contrast agent flow.

18 Claims, 2 Drawing Sheets

SYSTEM SCAN TIMING BY ULTRASOUND CONTRAST AGENT STUDY

BACKGROUND

The present embodiments relate to contrast agent imaging. In particular, timing of scan acquisition is provided for medical diagnostic contrast agent imaging.

Contrast agents are used in various types of medical diagnostic imaging. For ultrasound, the contrast agents are microspheres that reflect acoustic energy. The flow of contrast agents into a region (inflow or wash-in) and out of the region (outflow or wash-out) may be monitored with ultrasound scanning. The inflow and outflow may assist in diagnosis of problems in the circulatory system of the patient. Perfusion of contrast agents may be used to assist diagnosis of organs of the patient. Ultrasound scanning occurs sufficiently rapidly compared to the flow of the contrast agents to allow monitoring of the inflow and outflow. However, the microspheres may collapse due to the acoustic energy used for scanning, and ultrasound imaging may have relatively poor signal-to-noise ratio as compared to other types of scanning.

For magnetic resonance (MR) imaging, the contrast agents are gadolinium-based materials. MR scanning may occur relatively slowly as compared to the flow of contrast agents. A given scan for MR imaging takes sufficiently long relative to the movement of contrast agents that tracking inflow or outflow may be unreliable in some situations. The MR scan process may extend over a period in which different concentrations of contrast agent occur within a region, providing poor temporal resolution.

For computed tomography (CT) imaging, the contrast agents are iodine-based materials. CT scans may be performed relatively rapidly compared to the rate of flow. To monitor the flow, multiple CT scans are performed so that the inflow and/or outflow are not missed. However, scanning multiple times with CT results in increased radiation dose. This may be a concern particularly where scans are performed before contrast agents even arrive at and/or after leaving the scan region in order to not miss the arrival or outflow.

BRIEF SUMMARY

By way of introduction, the preferred embodiments described below include methods, systems, instructions, and computer readable media for scan timing. Ultrasound is used to determine timing of contrast agent inflow and/or outflow. The timing based on the ultrasound scanning controls scanning for MR or CT imaging. The MR or CT imaging for MR or CT contrast agents may be synchronized using the ultrasound contrast agent flow.

In a first aspect, a method is provided for scan timing. A first region of a patient is scanned with ultrasound. Ultrasound contrast agents in the first region are detected from the scanning. A timing of the detection of the ultrasound contrast agents in the first region is determined. The first region or a second region of the patient is scanned with a magnetic resonance or computed tomography system. The scanning with the magnetic resonance or computed tomography system is triggered based on the timing.

In a second aspect, a system is provided for scan timing. An ultrasound scanner is configured to monitor first contrast agents in a patient. An imaging system other than the ultrasound scanner is configured to monitor second contrast agents in the patient. An interface connects between the ultrasound scanner and the imaging system. The imaging system is configured to time acquisition of data representing the second contrast agents where the timing of the acquisition is a function of data representing the first contrast agents from the ultrasound scanner.

In a third aspect, a non-transitory computer readable storage medium has stored therein data representing instructions executable by a programmed processor for contrast agent imaging. The storage medium includes instructions for timing acquisition of a magnetic resonance or computer tomography contrast agent image, the timing based on contrast agents detected with ultrasound, and acquiring the contrast agent image in response to the timing.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

For MR or CT imaging, the arrival of an MR or CT contrast agent bolus in a region is of interest, such as for angiographic scans. In MR or CT, such detection of contrast agent arrival may be accomplished, but poses challenges including low sampling speed in MR and ionizing doses in CT.

MR or CT acquisition timing is established using ultrasound contrast agent detection. The combination of CT or MR and ultrasound imaging of contrast agents is used as one system to measure and/or calibrate for the use of contrast agents during scanning. The scanning time adapts for each patient's conditions and/or characteristics. Ultrasound provides timing information by tracking the arrival, wash-in and/or wash-out time of an ultrasound contrast agent. This timing is used for the MR or CT scan.

In one approach, the MR or CT timing is calibrated to the patient in their current state. Ultrasound contrast agent is injected to form a test bolus. The time from injection for the test bolus to reach, peak, or pass through the region of interest is used for the MR or CT scanning. After injection of the MR or CT contrast agent, the scanning by the MR or CT system begins at a time established by the time for the test bolus to have reached, peaked, or passed through the region of interest.

Rather than or in addition to calibration, real-time detection is used. Detection of ultrasound contrast agent by an ultrasound system triggers the acquisition of the MR or CT scan for the bolus of MR or CT contrast agents. Rather than using a separate test bolus, the ultrasound and MR or CT contrast agents are injected in quick succession or are mixed.

In either approach, custom scanning is provided for every patient. The timing of MR or CT scans is individualized. The timing of contrast agent scans for patients with different conditions and/or flow is optimized to the patient. Using this timing may reduce the radiation exposure to the patient, time slower acquisition to acquire the data of interest, and/or improve the scanning speed and resolution of the region of interest.

Figure 1:
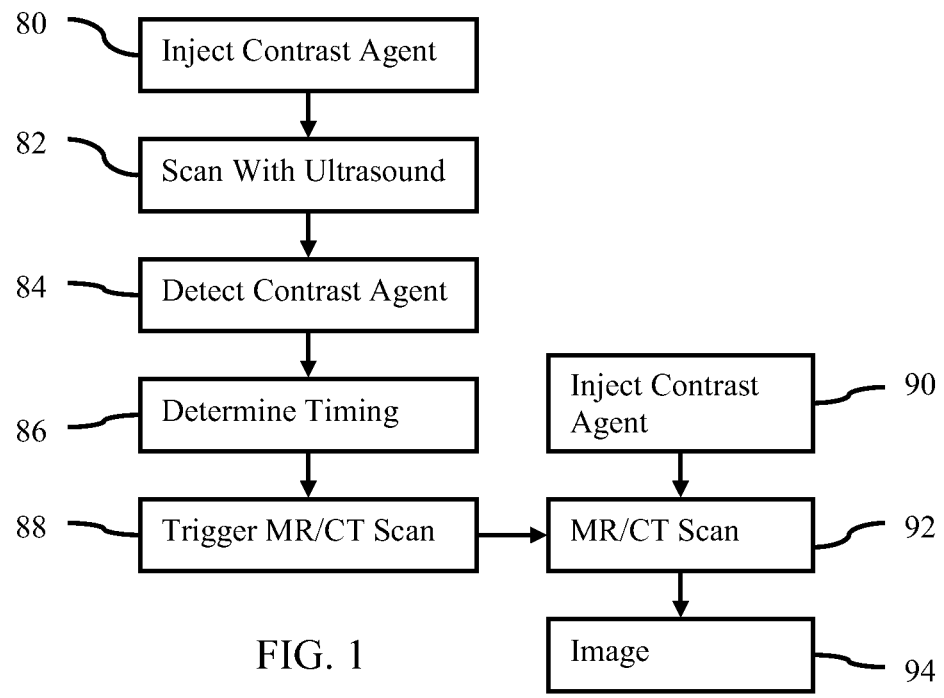
FIG. 1 is a flow chart diagram of one embodiment of a method for scan timing for contrast agent imaging.

FIG. 1 shows one embodiment of a method for scan timing in contrast agent imaging. The method is implemented with the system of FIG. 4, the system of FIG. 5, or a different system. An ultrasound scanner is used with an MR or CT scanner. Other imaging modalities than MR or CT may be used.

The acts are performed in the order shown or a different order. Additional, different or fewer acts may be provided. For example, act 94 is not performed.

The method uses timing determined with ultrasound scanning for contrast agents to trigger MR or CT scanning for contrast agents. Triggering is used to start, stop, or control the duration of the scanning. The scanning may be performed for calibration timing. Using ultrasound, the time for contrast agents to reach a region of interest from injection is calculated. The time is used to trigger MR or CT scanning after later injection of MR or CT contrast agents. The scanning may alternatively or additionally be performed for real-time timing. Using a mix of types of contrast agent in one bolus or injecting different types of contrast agents in rapid succession, the detection of ultrasound contrast agents is used to start the MR or CT scanning.

The start and/or end time of the MR or CT scan is based on the timing determined from the ultrasound scan. Alternatively or additionally, the duration of the MR or CT scan is based on the timing determined from the ultrasound scan. The contrast agents may take longer to flow to some regions than others. By detecting this difference using ultrasound, the difference may be used to optimize the duration or sequence for MR or CT scanning.

For use with MR or CT scanning, an acoustic array of elements is positioned against or within the patient. For MR, the acoustic array may be within a bore of a MR system or just outside the bore. The array is positioned on the patient bed or on the patient. When the patient is moved into the bore for MR imaging, the array may also moved within or may be within the bore. The acoustic array and any associated electronics are shielded and used in an interleaved manner with the MR scans to limit electromagnetic interference.

In act 80, ultrasound contrast agent is injected into the patient. Using an intravenous catheter, syringe, or other device, a bolus of contrast agent is injected. A pump or manual force may be used to force the bolus into the circulatory system of the patient.

The ultrasound contrast agent is any now know or later developed contrast agent. For example, the contrast agent is a plurality of microspheres surrounding gas. The microspheres may be coated.

The location of injection may be anywhere in or on the patient. In one embodiment, the bolus is injected within a vein in the leg of the patient. Injections through a catheter at or near the heart may be used in other embodiments.

In act 82, a region of a patient is scanned with ultrasound. The region is selected by image processing or by the user. For example, the user positions the transducer to scan the heart, arteries, veins, other portion of the circulatory system, or combinations thereof. The transducer may be positioned manually or robotically to scan veins and/or arteries in the leg of the patient. The transducer may be positioned to scan the carotid artery in the neck of the patient. The region of interest is established by directing the transducer to the desired scan plane or volume.

The region of interest may be further specified by detecting locations of interest within the field of view. For example, automated or manual detection of flow regions is performed. The user may input a box or other region of interest on an image.

The region of interest identification and scanning is performed after injecting the contrast agent in act 80. The region of interest identification and scanning may be performed before injecting. For example, the patient is scanned to find the region of interest prior to injection. After designating the region of interest, the transducer array is maintained in position and contrast agents are injected in act 80. Scanning continues to be performed during and after injection.

The patient is scanned by transmission of acoustic energy to the region of interest and receiving echoes responsive to the transmitting from the region of interest. The scanning is for a two-dimensional area or a three-dimensional volume. Any type of scan for detecting contrast agents may be used, such as for color Doppler, power Doppler, or B-mode.

The volume or area is scanned with electronic, mechanical, or both electronic and mechanical steering. A plurality of sequential transmit and receive events are performed to scan with ultrasound. In one example, broad transmit beams are formed for receiving respective pluralities of receive beams (e.g., receive sixteen or more receive beams in parallel in response to each transmit beam). Any scan format may be used, such as linear, sector, or Vector®.

To scan a volume rapidly (i.e., higher temporal resolution), a single pulse technique is used. For example, B-mode detection determines the intensity of the echoes for a given location in response to a single transmit beam. A pulse of acoustic energy is generated from one or more elements of a transducer. Each element generates acoustic energy for the pulse in response to electrical waveforms. Each electrical waveform may include one or more cycles, such as 1.5 cycles. Multiple transmit pulses are generated for scanning different locations in the volume. Other single pulse techniques may be used.

In other embodiments, multiple pulse detection may be used, such as receiving along a given scan line multiple times in response to multiple transmit pulses. Multiple pulse detection includes Doppler detection or phase inversion imaging. Combinations may be provided, such as scanning one portion of the volume with single pulses and another portion with multiple pulses per receive scan line.

The temporal resolution may be increased by using fewer receive and/or transmit scan lines with or without sparse sampling. Low spatial resolution allows for fewer transmit and respective receive events to scan the entire volume. Lowering the spatial resolution increases the frame rate. Other approaches, such as transmission with larger or more spread out wave fronts and more parallel receive beamformation, may be used to increase the frame rate for the volume scan.

Ultrasound data is received in response to the transmit pulses. Acoustic echoes reflect back to the transducer array or elements. The elements convert the acoustic echoes into electrical energy. The received ultrasound data is channel data output for each element, beamformed data, or detected data. For example, the ultrasound data is beamformed data representing one or more (e.g., 16) receive scan lines. The ultrasound data is formed from analog information or digital samples.

The transmitting and receiving are repeated sequentially to scan the volume or area. Alternatively, a single transmit or broad beam transmit may be used. A frame of data representing the entire volume is acquired in response to one transmission. For multiple pulse detection techniques, the transmission for scanning the entire volume may be repeated.

For ultrasound scanning while also performing MR or CT scanning, the scans may be operated independently of each other. Simultaneous scanning may be provided. In one embodiment, the scanning and receiving with ultrasound is interleaved with scanning with MR or CT. Any interleaving may be performed, such as scanning the volume partially, one time, or a plurality of times for each of the ultrasound and the MR or CT scans. In one embodiment, the ultrasound scanning is performed without MR or CT scans to establish the timing, and then CT or MR scans are performed without ultrasound scans based on the timing.

The ultrasound data is acquired repetitively. Data representing the region of interest at different times is repetitively acquired to monitor for the ultrasound contrast agents. For example, a succession of ultrasound images is acquired during or before MR or CT imaging and while contrast agents are administered. For calibration, the ultrasound images or data are acquired while the ultrasound contrast agent is administered. For real-time triggering, the ultrasound images or data are acquired while both ultrasound and MR or CT contrast agents are administered.

In one embodiment, the scan is performed multiple times. For example, the volume is scanned a plurality of times during a portion of a heart cycle. As another example, the volume is scanned a plurality of times during one or more heart cycles. Any frame rate may be provided, such as scanning 20, 30, or more times in a second or in a heart cycle. Scanning and receiving may be performed for other physiological cycles, such as the breathing cycle.

In act 84, ultrasound contrast agents in the region of interest are detected from the ultrasound scanning. The scanning may begin anytime before contrast agents enter the region of interest or before the contrast agent event of interest. As the scanning repeats, the entry or inflow of contrast agents may be detected. By detecting contrast agents in the region, the initial inflow, continuing inflow, outflow, and/or complete outflow may be detected.

The number of locations associated with contrast agents may be used to determine the initial inflow or completion of outflow. For example, when a threshold signal strength from an aggregate of detected contrast agents is detected, the initial inflow may be detected. The peak number of locations associated with contrast agent may indicate the completion of inflow and the beginning of outflow. Any technique for designating relative times at which events occur may be used.

The inflow and outflow occurrences may be detected at different times and/or for different parts of the region of interest. For example, the contrast agent may wash out of an artery in the leg before inflow and/or outflow in a vein where both the artery and vein are in the region of interest. Similarly, different inflow and outflow timing may occur in the heart.

The detection of the times of inflow and/or outflow relies on detection of contrast agents. The contrast agents may be detected with ultrasound using Doppler, B-mode or other imaging techniques. Contrast agents may be detected in response to single pulses for each scan line, such as using B-mode or intensity detection. To distinguish contrast agent response from tissue or fluid response, filtering may be used.

For example, contrast agents may have a stronger response at a harmonic (e.g., second or higher or fractional harmonic) of a fundamental transmit frequency than tissue or fluid. A difference in image intensity over time may be used to distinguish contrast agents from tissue or fluid since the contrast agent is generally transient and the tissue and fluid response are not.

Multiple pulse techniques may be used, such as transmitting with phase differences and adding or subtracting the responses to distinguish contrast agents from tissue or fluid. Phase inversion using two transmit pulses with opposite phase and combining the received signals may be used. In addition or alternative to different phases and/or amplitudes for transmitted pulses, different weights of the receive signals may be used.

In one embodiment, a non-linear fundamental response of the contrast agents is detected. The detection relies on combinations of signals from a plurality of transmit pulses. The received echoes from each transmission are combined to detect contrast agent response. For example, three or more receive signals representing a same location are combined to determine the nonlinear fundamental response at the location. The corresponding transmit pulses have different phases and amplitudes. Nonlinear fundamental response is greater for contrast agents than tissue, so provides good specificity. Other contrast agent detection may be used.

Use of multiple pulses may be slower than single pulse detection. For example, using three transmit pulses with different phases and/or amplitudes and combining the responsive echo signals scans three times slower than single pulse B-mode detection for a same spatial resolution and scan size. Two pulse-based techniques are twice as slow as corresponding single pulse B-mode or filtered harmonic B-mode techniques.

In act 86, timing of the detection of the ultrasound contrast agents is determined. The timing is of wash-in, wash-out, arrival, or completion. Any threshold number of fluid locations, average response from the fluid locations, or other calculation of contrast agent density or presence may be used.

The timing is relative to any event. For example, the timing is of the occurrence itself. In a real-time triggering approach, the time at which contrast agent is detected at the location or locations of interest is used. As another example, the timing is relative to an initial event, such as the injection of the contrast agents. The amount of time for the contrast agent bolus from injection until occurrence of the event of interest in the region of interest is calculated. For calibration, the time from the injection of the bolus of ultrasound contrast agents into the patient to initial detection of the ultrasound contrast agents at the region is used. The calibration may be for the peak or other event depending on the desired MR or CT contrast agent study.

The timing for multiple events may be determined. For example, the arrival of contrast agents in the region of interest and the exit of contrast agents in the region of interest is determined. The timing of the arrival, wash-in and wash-out time of the contrast agent may be determined. In one embodiment, the timing is for duration. The time from beginning to end of wash-in, wash-out, or both is determined.

The timing may be location specific. For example, the region of interest may include locations with different arrival, inflow, outflow, or other times. The timing is determined for the sub-region of interest. In one embodiment, the timing is for a period from arrival at any location in the region of interest and exit from the last location in the region of interest. In another embodiment, the timing is for arrival at a specific location or locations, exit from the specific location or locations, and/or a period between the two. The timings may be different for different blood vessels in the field of view or region of interest. For example, if some blood vessels fill much later than the main vessel, the ultrasound scanning and detection indicate the timing for the desired vessel or vessels, allowing the MR or CT acquisition to spend more time, have a start time, or have an end time for the desired location in order to not miss the dynamics of the late filling vessels.

In act 90, contrast agents for MR or CT scanning are injected. Any now known or later developed MR contrast agent may be used, such as gadolinium-based contrast agents. Any now known or later developed CT contrast agents may be used, such as iodine-based contrast agents.

The same location, pump, technique, and device may be used for the MR or CT contrast agents as for the ultrasound contrast agents. In one embodiment, the MR or CT contrast agents and the ultrasound contrast agents are mixed together. In another embodiment, contrast agents detectable by both ultrasound and MR or CT are used, such as microspheres made of or enclosing iodine or gadolinium-based materials.

In an alternative embodiment, different pumps or devices are used. The location of injection is the same or close. The timing of the injections may be the same. Given different locations of injection, injecting at the same time may lead to one bolus (e.g., ultrasound contrast agent) arriving at the region of interest earlier. Sequential injection at the same or different locations may be used for the same differential arrival. This sequential provision of the different types of contrast agents occurs on a time scale small compared to the time for the boluses to progress to the region of interest.

In another embodiment for calibration, the injections are not timed relative to each other. The ultrasound contrast agents are injected for determining the timing. The timing is then used whenever the MR or CT contrast agents are later injected.

In act 88, the timing of acquisition of MR or CT contrast agent data is performed. Using the timing information based on contrast agents detected with ultrasound, the timing of the MR or CT acquisition is controlled. The MR or CT acquisition of act 92 is synchronized with the MR or CT contrast agent based on the timing from the ultrasound contrast agents.

The acquisition timing is performed by triggering the MR or CT scanning based on the timing determined in act 86. The triggering is by a control input to the MR or CT system. Alternatively, the triggering is by an internal calculation or control of the MR or CT system. Hardware and/or software are used to control the timing. Whether external or internal, the timing from the ultrasound contrast agent detection is used to control when the MR or CT scan starts, control the duration of the MR or CT scan, control the MR or CT scan interval (e.g., time between scans), control when the MR or CT scan ends, or combinations thereof. The start, stop, duration, and/or interval may be triggered.

Figure 2:
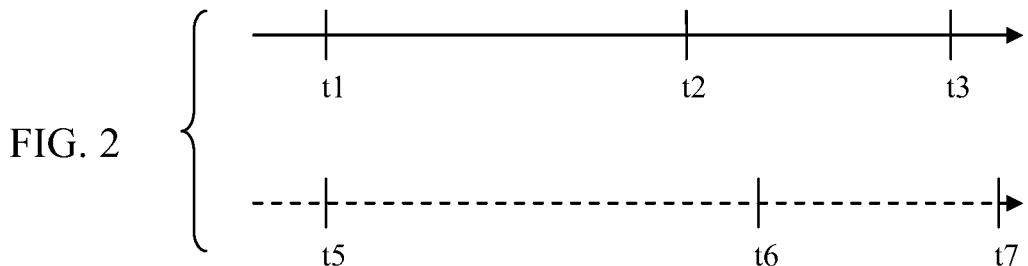
FIG. 2 illustrates example timing relationships between ultrasound and MR/CT scans for calibration of scan timing in contrast agent studies.

In one embodiment represented in FIG. 2, the triggering is calibrated. In the timeline represented by the solid line, ultrasound contrast agent timing is detected. At time t1, ultrasound contrast agents are injected. At time t2, ultrasound contrast agents are detected at a region of interest. At time t3, the complete wash-out of contrast agents is detected. These acts are performed prior to the MR or CT timeline represented by the dashed line.

For the MR or CT timeline (dashed line), contrast agents are injected at time t5. Based on the relative locations of injection and/or regions of interest, the time until MR or CT contrast agents enter the MR or CT region of interest is based on the time difference t1-t2 from the ultrasound detection. This time (e.g., contrast agent travel time as measured using the contrast agents plus any offset for location or agent differences) is added to the time of MR or CT contrast agent injection, resulting in time t6. Alternatively, the time t6 is a same period after injection from time t5 as time t2 is from time t1.

In some embodiments, the location of detection of the contrast agents is different than the location of the MR or CT region of interest. For example, the CT or MR scan is of the brain, but the contrast agent detection occurred at the neck. This difference is accounted for in the time difference, such as adding a temporal offset, providing for the relative time location of t6 from time t5 as compared to time t1 and time t2. The triggering to acquire the MR or CT data occurs the same or different period after the injection as the contrast agent. The occurrence of the trigger is based on the amount of time determined with ultrasound scanning, with or without offsets for other reasons.

FIG. 2 also represents setting duration of the MR or CT scanning based on timing from the ultrasound contrast agent detection. The period from time t6 to t7 represents the scan period during which one or more scans are performed. The period t7-t6 is based on the period of inflow, outflow, or both determined from the period of times t2-t3 with ultrasound contrast agent. The difference in relative time between t2 and t6 and between t3 and t7 is the same or different and based on the same or different temporal or spatial offset. The duration may be based on the ultrasound and MR or CT regions being at a same or different location. The duration is set to provide for MR or CT scanning appropriate for a desired location of the patient since contrast agents in that patient are used to establish the timing. The timing and associated triggering anticipates the life of contrast agent in different blood vessels.

The triggering for the duration may be used without the triggering for starting or ending. Similarly, the triggering for starting or ending may be used without the triggering for duration.

Figure 3:
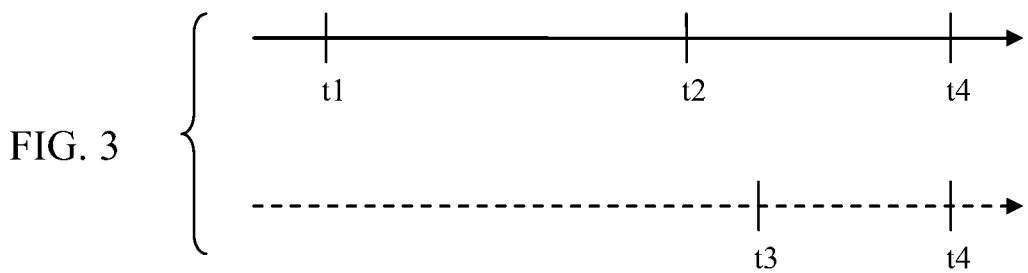
FIG. 3 illustrates example timing relationships between ultrasound and MR/CT scans for real-time triggering in contrast agent studies.

FIG. 3 represents real-time triggering. The timing of the MR or CT scanning is based on timing as detected. The detection of ultrasound contrast agents at time t2 after the injection at time t1 is performed. The MR or CT timeline (dashed line) and the ultrasound timeline (solid line) represent the same time rather than sequential timelines of FIG. 2. The MR or CT scan is triggered based on the detection at time t2 without determination of the period from injection. The MR or CT timeline shows triggering at time t3. Time t3 is shown as after time t2, but may be time t2 in other embodiments. The difference between t2 and t3 is due to spatial or temporal offset. The offset is purposeful, such as associated with different locations for injection or detection, associated with sequential injection (e.g., one right after the other), and/or associated with processing delay to trigger from detection. A counter counting down or up may be used to implement the offset. When the count completes, the MR or CT scanning is triggered. The time of injection of the CT or MR contrast agent may not be used as a reference (other than for determining the offset), so is not shown.

The duration for the MR or CT timeline is shown as shorter. For example, the time t4 of detection of complete inflow, complete outflow or other event for ultrasound contrast agent is used to trigger ceasing of the MR or CT scanning. Different times for the duration may be used.

For triggering MR scanning, the scan is triggered to capture the desired arrival, wash-in, wash-out or combinations thereof. The MR scanning requires a certain time period. To avoid most or a substantial portion of the scan being at an undesired time relative to the contrast agents, the timing of the start of the MR scan is triggered. Given the scan time, the trigger may be performed based on any level of contrast agents detected with ultrasound scanning. The interval for repetitive scanning may be set based on the rate of ultrasound contrast agent flow, the duration of the event of interest (e.g., in or outflow or both), or other timing. The physiological timing information is used to control the speed of MR imaging.

For CT scanning, the triggering may be used for start, stop, interval, or duration. The CT triggering may avoid radiation to monitor when a contrast agent event is going to occur. Ultrasound scanning monitors for the desired event and is used to trigger the CT scanning. Lower radiation dose may result where CT scanning is used to sample the CT contrast agents at appropriate times and not at other times.

In act 92, the MR or CT system scans the patient. When triggered, data representing the MR or CT contrast agents, tissue, and/or fluid (e.g., blood) of the patient is acquired. The trigger indicates a start time of the scan. The trigger signal may instead trigger a delay timer for the start of the scan.

The region of interest used for detecting contrast agents by the ultrasound scanner is scanned. A larger or more inclusive region may be scanned. The larger region includes all of or a part of the ultrasound region of interest. In alternative embodiments, the MR or CT scans are for a different region of the patient than the region used for detecting ultrasound contrast agent. For example, the MR or CT scan is of a vein and the ultrasound scan is of an artery. As another example, the ultrasound scan is of an upstream location of a vessel and the MR or CT scan is of a downstream location.

The MR or CT region of interest may be larger or smaller than the ultrasound region of interest. The MR, CT, and/or ultrasound regions of interest may be smaller than the respective fields of view. Alternatively, one or more of the regions of interest are the fields of view of the scanning. In other embodiments, multiple regions of interest for one or more of the types of scanning are used. The same or different timing may be used for each region of interest.

The MR or CT scan is of a plane or volume. The same or different sampling density or resolution is used for the ultrasound scanning and the MR or CT scanning.

For MR scanning, a sequence of radio frequency pulses in controlled magnetic fields is used to generate a response from selected molecules. Any MR sequence may be used. The frequency of the pulses, the sequence used, and/or the magnetic fields are set based on the type of molecule or material to be detected. For contrast agents, the appropriate settings are provided. Any now known or later developed MR scanning for MR contrast agents may be used. The scanning may also be to detect tissue and/or fluids of the patient. The same sequence or a different sequence of pulses is used.

The radio frequency pulses are applied by a body coil surrounding a bore of the MR system. Alternatively or additionally, one or more local coils are used for greater signal-to-noise ratio. The local coils are positioned on, closer, or in the patient. The radio frequency pulses are generated by the local coils or the body coil. The local coils receive the signals generated by the changing spins of the molecules.

The signals received from the MR scanning are in k-space. Using Fourier transforms, the data may be transformed to object or real-space. The transform provides MR data representing the contrast agents, tissue, and/or fluid. The MR data represents an area or volume of the patient, such as for an MR cranial scan.

For CT scanning, an x-ray source is positioned opposite an x-ray detector. The patient is positioned between the x-ray source and detector. By rotating the x-ray source and detector about the patient, a sequence of projection data is detected. For a given detection, an amplitude of the detected x-rays represents the various tissues, fluids, and/or contrast agents between the x-ray source and the pixel of the detector. The detector may be a one or two-dimensional detector. Each datum represents a line or projection through the patient at the given position of the x-ray source and detector relative to the patient.

The x-ray source and detector may be positioned at different locations to scan the patient. By rotating and translating, a volume of the patient may be scanned from different directions. By rotating or translating, a plane or area of the patient may be scanned from different directions.

Using tomography, the projection data is converted into real or object-space data. Due to the sampling of locations in the patient from different angles, the projection data may be fit to a model of the x-ray response from the patient. The fit provides magnitudes of x-ray signal for each location in the patient. The contrast agents may cause a greater reduction in the x-ray signal passing through, similar to bone. Since the contrast agent flows within the circulatory system, the flow in the circulatory system may be highlighted relative to tissue.

Using either MR or CT scanning, data representing contrast agents is acquired. The timing from the ultrasound scanning is used to acquire the MR or CT data. The MR or CT scanning is performed at the appropriate time or times for the flow of contrast agents. This may avoid scanning at unneeded times. The scanning may be directed or steered to locations likely to have contrast agents at any given time, such as through a sequence of regions of interest. The calibrated or real-time timing information derived from the ultrasound contrast agent helps optimize the MR or CT scanning.

As represented by the time between t5 and t6 and after t7 in FIG. 2 or the time before t and after t4 in FIG. 3, scanning at times in which contrast agent is not or is not likely in the region of interest may be avoided. This may limit radiation dose. Similarly, the start time for MR scans may be timed to occur at the desired time relative to the contrast agent bolus position, providing more diagnostic information. The sampling speed for MR may be increased, and the radiation exposure in CT may be decreased.

The acquired scan data may be used for calculating contrast agent information. For example, the rate, relative timing, peak amount or other characteristic of contrast agent inflow and/or outflow is quantified. The MR or CT data is used to determine the quantities. The quantification may be provided for different locations to provide relative information. Any contrast agent study may be used.

The acquired scan data may be used to generate an image in act 94. The image is of the quantity or quantities calculated for the contrast agent study. The values are displayed as text or a graph. For example, a graph of average number or intensity of contrast agents in a region over time is displayed. A value representing the rate of inflow or outflow may be displayed with or without the graph.

In one embodiment, an image of the contrast agent is generated. Any now known or later developed MR or CT contrast agent imaging may be used. For example, an image representing a scan plane or a plane through a scan volume is generated. The intensity or other detected characteristics at different locations in the plane are used to generate image data or values for pixels. As another example, data representing a volume is rendered using projection or surface rendering. The image may be overlaid with or combined with images from other sources, such as overlaying detected contrast agent with tissue information. The contrast agent information may be rendered as more opaque and the tissue more transparent.

The image represents a point, line, area or volume. Images for multiple planes may be generated and displayed at a same time or sequentially. Any imaging format may be used. The image is of a region of interest, a field of view, or other location. Segmenting may be used, such as extracting data associated with a desired organ or region and imaging from the extracted data. Color or black and white imaging is provided.

Ultrasound images may be generated. Ultrasound images of a quantity or quantities representing contrast agents in the region of interest may be displayed. Values and/or graphs are generated based on the detected ultrasound contrast agents. The values or graphs may be combined with values and/or graphs from MR or CT contrast agents or displayed separately. For example, an average inflow time or rate is calculated from ultrasound and MR or CT contrast agent time or rate values.

A sequence of images may be generated to represent the ultrasound contrast agent arriving and flowing through region of interest. A single image of tissue, fluid, and/or contrast agent may be generated. Any now known or later developed contrast agent, tissue, fluid, or combined ultrasound imaging may be used.

The image or images of the ultrasound contrast agent may be displayed at the same or different times than the image or images of MR or CT contrast agent. Simultaneous display is provided with the images adjacent to each other. In one embodiment, the images are combined, such as averaging values for the same locations or overlaying one type of image over another type of image (e.g., CT or MR contrast agent modulated to color and ultrasound contrast agent modulated to intensity).

For combination, the ultrasound coordinates may be registered with the MR or CT coordinates. The registration provides data representing the same locations. The registration may be based on position sensors, data correlation, or both. For example, the MR tissue data is processed to emulate ultrasound. The emulation may be correlated with the ultrasound B-mode data to determine a transform relating the two coordinate systems. Rigid or non-rigid transforms may be used.

Figure 4:
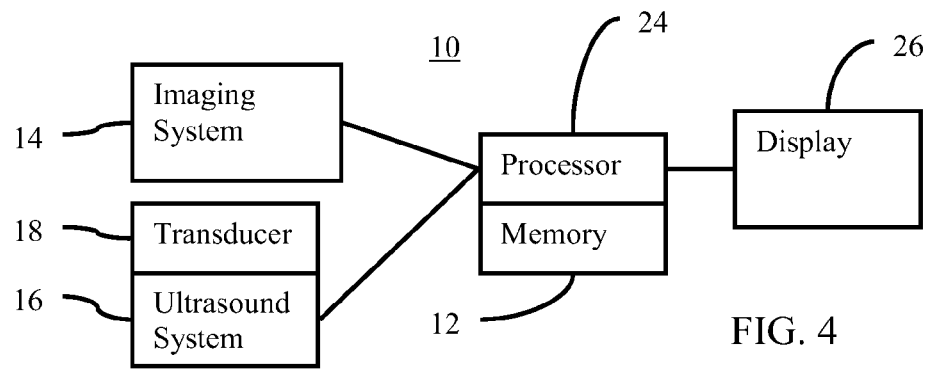
FIG. 4 is a block diagram of one embodiment of a system for scan timing using contrast agents.
Figure 5:
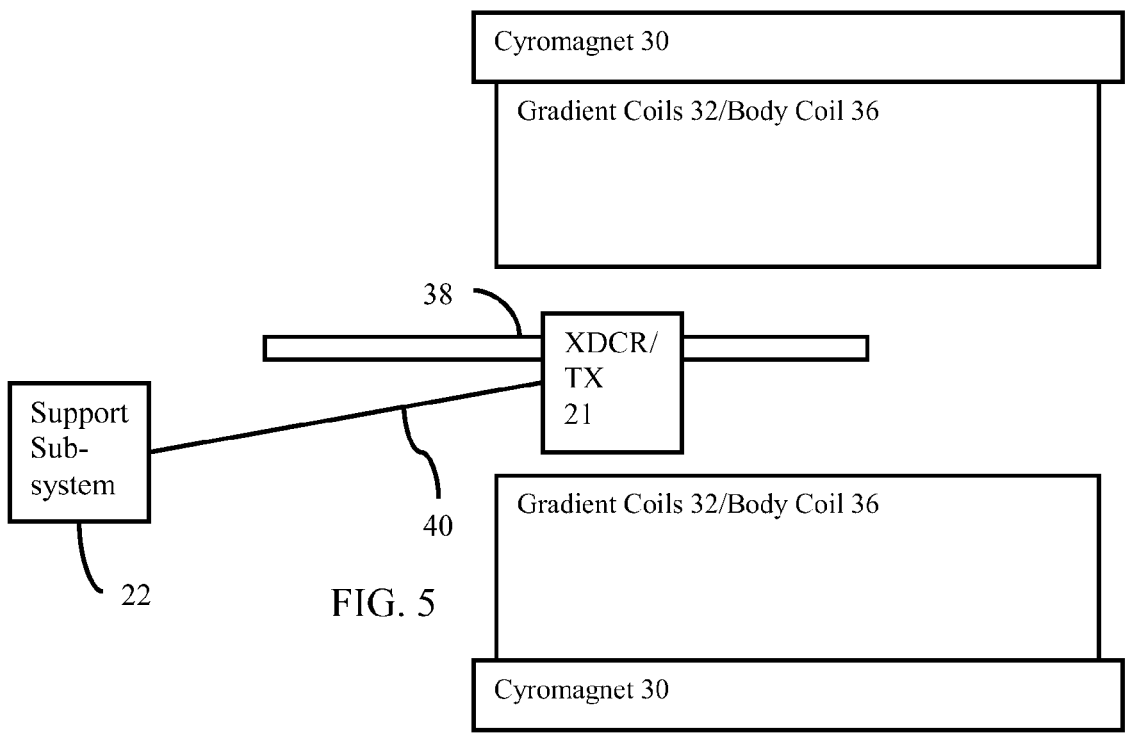
FIG. 5 is a combined MR and ultrasound system for timing scans, according to one embodiment of FIG. 4.

FIG. 4 shows a system 10 for scan timing in contrast agent studies. The system 10 includes a memory 12, an imaging system 14, an ultrasound system 16, a transducer 18, a processor 24, and a display 26. The ultrasound system 16 and the transducer 18 are for use with the imaging system. The ultrasound system 16 and the transducer 18 may be sub-divided into a sub-system 22 and an applicator 21, as shown in FIG. 5. FIG. 5 shows one example of positioning of the transducer 18 and the ultrasound system 16 relative to the imaging system 14 where the imaging system 14 is an MR system.

Additional, different, or fewer components may be provided. For example, a network or network connection is provided, such as for networking with a medical imaging network or data archival system. As another example, the processor 24, the memory 12, and/or the display 26 are not provided.

The memory 12, processor 24 and display 26 are part of a medical imaging system, such as the ultrasound system 16, imaging system 14, or other system. Alternatively, the memory 12, processor 24 and display 26 are part of an archival and/or image processing system, such as associated with a medical records database workstation or server. In other embodiments, the memory 12, processor 24 and display 26 are a personal computer, such as desktop or laptop, a workstation, a server, a network, or combinations thereof.

The processor 24 is an interface between the imaging system 14 and the ultrasound system 16. The interface is hardware and/or software based. For example, the processor 24 is part of a network connection or interface card. As another example, the processor 24 is a control processor or server. In yet another example, the processor 24 connects to one or both of the imaging system 14 and the ultrasound system 16 through a dedicated connection for determining and/or controlling timing of scanning. The connection may be over a network, on a bus, wireless, wired, or other now known or later developed connection. In alternative embodiments, the processor 24 is part of the ultrasound or imaging systems 16, 14 allowing a direct connection between the two systems.

An input to the processor 24, the imaging system 14, and/or the ultrasound system 16 connects or is connectable with an injection pump for contrast agents. The system 10 controls the injection of the ultrasound and/or MR or CT contrast agents. The control allows for timing calibration. Alternatively, the user input or interface associated with the processor 24, the imaging system 14, and/or the ultrasound system 16 may provide for manual input by the user to indicate a time of injection. In other embodiments, such as for real-time detection and timing, the time of injection is not needed to determine the timing. The injection pump may be operated without connection to the system 10.

The display 26 is a monitor, LCD, projector, plasma display, CRT, printer, or other now known or later developed devise for outputting visual information. The display 26 receives images, graphics, or other information from the processor 24, memory 12, imaging system 14, or ultrasound system 16. The display 26 may be used for contrast agent imaging and a user interface to configure operation of the system 10.

In one embodiment, the imaging system 14 is used to generate one or more images representing contrast agents in a patient for display on the display 26. For example, an image or images rendered from a three-dimensional data set of MR or CT information is provided. A multi-planar reconstruction may be provided. The user may indicate a region of interest for contrast agent study of the patient on the image. Alternatively, the processor 24 identifies the region of interest.

The ultrasound system 16 is any now known or later developed ultrasound system. For example, the ultrasound system 16 includes the transducer 18 for converting between acoustic and electrical energies. A transmit beamformer relatively delays and apodizes signals for different elements of the transducer 18. The ultrasound system 16 includes a receive beamformer for sampling the field of view and receiving ultrasound data.

The transducer 18 is an array of elements, such as piezoelectric or capacitive elements. The array is a one-dimensional or multi-dimensional distribution of elements. For example, the transducer 18 is a two-dimensional array for scanning a volume electronically. As another example, the transducer 18 is a wobbler transducer array for scanning in one dimension electronically and in another dimension mechanically. Other now known or later developed transducers 18 for mechanical and/or electrical steering of different planes may be provided. For example, a user may move a one dimensional array transducer manually or robotically to a new location for each plane.

The ultrasound system 16 uses transmit and receive beamformers for scanning a region with the transducer 18. In one embodiment, the transmit beamformer includes transmitters or waveform generators for generating electrical waveforms for each element of a transmit aperture. The waveforms are associated with phase and amplitude. The waveforms for a given transmit event may have the same or different phasing. The electrical waveforms are relatively weighted and delayed to form an acoustic beam with a desired phase and amplitude characteristic. For example, the transmit beamformer includes amplifiers, phase rotators, and/or controllers to generate sequential, steered pulses with the desired phase and amplitude in relation to other acoustic beams. Converging, diverging or planar beams may be used.

The receive beamformer may include delays, phase rotators, amplifiers, and/or adders for relatively delaying and summing received signals to form one or more receive beams with dynamic focusing. For example, using shared processing, separate processing, or combinations thereof, a plurality (e.g., tens or hundreds) of parallel receive beamformers are provided to form a respective plurality of receive beams in response to a given transmit beam. Alternatively, the beamformer 14 includes a processor for Fourier or other analysis of received signals to generate samples representing different spatial locations of the scanned region.

The transducer 18 and beamformers are configured to scan an area or volume. The beamformers are controlled or programmed to perform the scan. The beamformer parameters, such as relative delays and/or phasing for focus, apodization, beam amplitude, beam phase, frequency, or others, are set. The aperture for transmit and the aperture for receive on the transducer 18 is set. The beamformer and transducer 18 are used to generate the waveforms for the aperture and convert the waveforms to acoustic energy for transmitting the beam, and used to receive acoustic energy at the receive aperture, convert the acoustic energy to electrical energy, and beamform the received electrical signals.

A volume or planar scan may be performed using any pattern or distribution of scan lines. In one embodiment, an acquisition scan plane is positioned within a three-dimensional region. Acoustic energy is transmitted in any of various now known or later developed scan patterns along the scan plane for acquiring data. The scan plane is then altered to another location in the volume or sub-volume and scanned. Alternatively, a planar scan is performed.

For a given volume or plane, the scans may be repeated. By repeating the scans, a sequence of frames of data is obtained. Each frame represents the three-dimensional scanned volume or two-dimensional scanned plane, but may only represent smaller regions within the field of view.

Ultrasound contrast agents are more likely destroyed by higher amplitude, greater scan line density, greater pulse repetition, lower frequency, and/or other parameter for increasing the destructive power. Due to phased array focusing, contrast agents at deeper and/or shallower depths may be subjected to less destruction. The focal point, amplitude, scan line density, pulse repetition, frequency and/or other parameter may be varied to avoid or limit destruction of contrast agents in the region of interest. Transmissions causing destruction may be provided for clearing a region for subsequent detection of ultrasound contrast agents and timing determination.

The ultrasound system 16 includes a detector. The detector is configured by hardware and/or software to detect from the beamformed data. Any detection may be used, such as B-mode, Doppler or color flow mode, harmonic mode, or other now known or later developed modes. B-mode and some harmonic modes use single pulse scan techniques for detection. The intensity of the received signals in the frequency band of interest is calculated. Multiple pulse techniques, such as flow mode estimation of velocity or energy, may be used.

In one embodiment, the detector is a contrast agent detector configured to detect response from contrast agents. The configuration is provided by software and/or hardware. The contrast agent detector is a B-mode detector, Doppler or flow estimator, contrast agents specific detector, or other now known or later developed device for detecting acoustic response of contrast agents. The contrast agent detector may include a filter, summer, memory, buffer, rectifier, or other components for combining data responsive to different transmissions.

The detected response may include other information, such as second harmonic, even harmonic, B-mode, velocity or power estimates including information from tissue, moving tissue, and/or blood. Alternatively, the detected response is specific to contrast agents, such as using a combination of receive signals responsive to transmit pulses with different phase and amplitude to detect contrast agent while limiting response from tissue. For example, the nonlinear fundamental response is detected by combining three or more receive signals responsive to transmit beams with different phasing and amplitude.

By repeating scanning, any ultrasound contrast agents in a patient are monitored. The region of interest is scanned multiple times. As the ultrasound contrast agent enters the region of interest, the contrast agents are detected. As the flow continues, the contrast agents are detected.

For use in real-time with the imaging system, the transducer 18 is left in situ during the imaging system scans. For MR scanning, the transducer 18 may be shielded. For CT scanning, the transducer 18 may be positioned to avoid interference or may be segmented out. The transducer 18 may be positioned to scan from a location avoiding interference or limiting interference with the scanning of the imaging system 14. For example, cranial scans are performed by the imaging system 14. The transducer 18 is positioned to scan the carotid artery for timing, thus leaving the transducer 18 substantially outside the imaging volume of the CT or MR device.

The imaging system 14 is a MR or CT scanner. Other non-ultrasound modalities may be used, such as positron emission tomography or single photon emission computed tomography.

As a CT scanner, the imaging system 14 includes an x-ray source and detector. A robotically controlled or positioned C-arm holds the x-ray source and detector. Collimators, filters or other CT scanner components may be provided. A processor, such as the processor 24, fits the projection data from the detector to an object model to determine the spatial locations of response to the x-rays.

FIG. 5 shows the imaging system 14 as an MR scanner. The magnetic resonance (MR) system includes a cyromagnet 30, gradient coil 32, and body coil 36 in an RF cabin, such as a room isolated by a Faraday cage. A tubular or laterally open examination subject bore encloses a field of view. A more open arrangement may be provided. A patient bed 38 (e.g., a patient gurney or table) supports an examination subject, such as a patient with or without one or more local coils. The patient bed 38 may be moved into the examination subject bore in order to generate images of the patient. Received signals may be transmitted by the local coil arrangement to the MR receiver via, for example, coaxial cable or radio link (e.g., via antennas) for localization.

Other parts of the MR system are provided within a same housing, within a same room (e.g., within the radio frequency cabin), within a same facility, or connected remotely. The other parts of the MR system may include local coils, cooling systems, pulse generation systems, image processing systems, and user interface systems. Any now known or later developed MR imaging system may be used. The location of the different components of the MR system is within or outside the RF cabin, such as the image processing, tomography, power generation, and user interface components being outside the RF cabin. Power cables, cooling lines, and communication cables connect the pulse generation, magnet control, and detection systems within the RF cabin with the components outside the RF cabin through a filter plate.

The MR system is configured by software, hardware, or both to acquire data representing a plane or volume in the patient. In order to examine the patient, different magnetic fields are temporally and spatially coordinated with one another for application to the patient. The cyromagnet 30 generates a strong static main magnetic field $B_0$ in the range of, for example, 0.2 Tesla to 3 Tesla or more. The main magnetic field $B_0$ is approximately homogeneous in the field of view.

The nuclear spins of atomic nuclei of the patient are excited via magnetic radio-frequency excitation pulses that are transmitted via a radio-frequency antenna, such as a whole body coil 36 and/or a local coil. Radio-frequency excitation pulses are generated, for example, by a pulse generation unit controlled by a pulse sequence control unit. After being amplified using a radio-frequency amplifier, the radio-frequency excitation pulses are routed to the body coil 36 and/or local coils. The body coil 36 is a single-part or includes multiple coils. The signals are at a given frequency band. For example, the MR frequency for a 3 Tesla system is about 123 MHz+/−500 KHz. Different center frequencies and/or bandwidths may be used.

The gradient coils 32 radiate magnetic gradient fields in the course of a measurement in order to produce selective layer excitation and for spatial encoding of the measurement signal. The gradient coils 32 are controlled by a gradient coil control unit that, like the pulse generation unit, is connected to the pulse sequence control unit.

The signals emitted by the excited nuclear spins are received by the local coil and/or body coil 36. In some MR tomography procedures, images having a high signal-to-noise ratio (SNR) may be recorded using local coil arrangements (e.g., loops, local coils). The local coil arrangements (e.g., antenna systems) are disposed in the immediate vicinity of the examination subject on (anterior), under (posterior), or in the patient. The received signals are amplified by associated radio-frequency preamplifiers, transmitted in analog or digitized form, and processed further and digitized by the MR receiver.

The recorded measured data is stored in digitized form as complex numeric values in a k-space matrix. A one or multi-dimensional Fourier transform reconstructs the object or patient space from the k-space matrix data. The processor 24 or another device performs the reconstruction.

The MR system may be configured for acquiring contrast agent information. MRI contrast agents alter the relaxation times of atoms within body tissues after intravenous administration. A radiofrequency pulse is applied causing atoms in contrast agents to spin and then relax after the pulse stops. This relaxation emits energy which is detected by the MR scanner. The difference in relaxation time and/or the signals from the contrast agents themselves may be detected.

The MR system may be configured to acquire different types of data. For example, the MR data represents the anatomy of the patient. The MR data represents the response to the magnetic fields and radio-frequency pulses of tissue. Any tissue may be represented, such as soft tissue, bone, or blood. The MR system may be configured for acquiring specialized functional or anatomic information. For example, T1-weighted, diffusion, thermometry, or T2-weighted MR data is acquired.

The ultrasound system 16 and the transducer 18 are adapted for use in the MR environment. Despite the MR system being susceptible to even very small electromagnetic interference, more than the transducer 18 may be positioned in the bore and corresponding main magnetic field. At least some active electronics or circuits may be provided with the transducer 18. For example, the transmit beamformer and a communications interface are provided with the transducer 18 in an applicator 21. Providing the transmit beamformer at the transducer 18 avoids electrical impedance concerns associated with long cabling. An array of many elements may be provided since a corresponding many coaxial cables are not needed, avoiding electromagnetic interference associated with the coaxial cables.

As represented in FIG. 5, a portion or sub-system 22 of the ultrasound system 16 is spaced from the MR system or at least the bore and main magnetic field. The sub-system 22 provides for user interface and high level or general control functions of ultrasound scanning. For example, the processor 24 is part of the sub-system 22. These control and user interface functions may be integrated into the MR system.

The connection 40 between the transducer 18 and the sub-system 22 may be one, two, or few number of cables. For example, the connection 40 is an optical cable or fiber optic cable for transmitting control signals to the transducer 18. Separate connections may be provided for trigger and/or mode selection, or the same cable is used. The connection 40 may include a pipe, tube, or hose for fluid.

The imaging system 14 is configured to monitor contrast agents in the patient. The contrast agents are monitored by scanning for the contrast agents. Using the timing from the ultrasound scanning, the timing of the monitoring is focused. The imaging system 14 scans the patient to detect contrast agents at the appropriate times.

The processor 24 is an interface between the ultrasound system 16 and the imaging system 14. The processor 24 is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for determining timing and/or triggering scanning. The processor 24 is a single device or multiple devices operating in serial, parallel, or separately. The processor 24 may be a main processor of a computer, such as a laptop or desktop computer, or may be a processor for handling tasks in a larger system, such as in an imaging system 14 or ultrasound system 16.

The processor 24 is configured by software and/or hardware. Hardware timing triggers may be used. Software based counters may be used. The processor 24 may be configured to trigger operation of the transducer 18 and/or the imaging system 14. The scanning of the imaging system 14 and the ultrasound system 16 may be interleaved based on control by the processor 24. The scanning from the different systems 14, 16 may be caused to occur at a same time.

The imaging system 14 is configured to time acquisition of data representing contrast agents. In response to a trigger signal generated by the processor 24, the imaging system 14 begins or arranges to begin scanning for contrast agents.

The processor 24 interfaces with the imaging system 14 to trigger the contrast agent scanning. The processor 24 is configured to time the acquisition or triggering of the acquisition based on data from the ultrasound system 16. The ultrasound contrast agent detection is used to determine timing for the imaging system 14. The detection of contrast agents by the ultrasound system 16 is used to determine the time of acquisition by the imaging system 14.

The processor 24 is configured to determine the time of acquisition based on one or more criteria. For example, the time of arrival from injection is used. The time for ultrasound contrast agents to travel from the injection location to the region of interest is calculated. MR or CT contrast agents may have the same or similar travel time. Alternatively, the processor 24 determines the MR or CT contrast agent travel time based on a ratio or other offset. For example, the MR contrast agent may need to also perfuse tissue, so a temporal offset is added to the travel time.

The time from injection or from other starting points (e.g., arrival) to other events may be used. For example, the processor 24 is configured to time from injection to a peak amount of contrast agent response for a wash-out MR or CT study.

In addition or alternative to calibrating the timing, ongoing detection may be used. The timing of the scanning by the imaging system 14 is based on current detection of contrast agents by the ultrasound system 16. The processor 24 is configured to interface between the two systems so that detection of a contrast agent event by the ultrasound system 16 triggers immediate or delayed scanning by the imaging system 14. For example, the ultrasound system 16 detects ultrasound contrast agents at a region of interest. Upon detection or after a further delay from the detection, the processor 24 sends a signal or causes the imaging system 14 to begin scanning. Other times than arrival may be used as the triggering event.

The processor 24 is configured to determine the duration of the scanning by the imaging system 14. The time for ultrasound contrast agents to wash-in, wash-out, or both is calculated from the detected ultrasound contrast agents. The time, with or without any positive or negative offset, is used to trigger an end to the scanning by the imaging system 14. The duration is set to last through the wash-in and/or wash-out.

The duration may be location specific, such as triggering scanning to begin based on contrast agents at one location and end scanning based on contrast agents at a different location. Separate triggering may be used for different locations. For example, the imaging system 14 scans different regions at different times. The timing for each region may be established, at least in part, based on the detection of ultrasound contrast agents in the respective regions.

The timing for ceasing may be used with or without triggering for starting the scanning. The detection of the ultrasound contrast agents may be used to end the scanning without having been used to begin the scanning. Alternatively, the imaging system 14 scans for a set amount of time or through a set sequence without using timing from the ultrasound contrast agents.

The memory 12 is a graphics processing memory, a video random access memory, a random access memory, system memory, random access memory, cache memory, hard drive, optical media, magnetic media, flash drive, buffer, database, combinations thereof, or other now known or later developed memory device for storing data. The memory 12 is part of the imaging system 14, part of the ultrasound system 16, part of a computer associated with the processor 24, part of a database, part of another system, or a standalone device.

The memory 12 stores one or more datasets representing a three-dimensional patient volume or a two-dimensional patient plane. The patient volume or plane is a region of the patient, such as a region within the chest, abdomen, leg, head, arm, or combinations thereof. The patient volume is a region scanned by the imaging system 14 and/or the ultrasound system 16.

Any type of data may be stored, such as medical image data or detected contrast agent data. The data represents the patient and/or contrast agents within the patient. Data derived from scan or detected data may be stored. For example, timing information is stored. As another example, a count for implementing or using the timing to trigger is stored. Times may be stored. Quantities representing any aspect of contrast agents may be stored, such as storing data representing a contrast agent return over time. Thresholds or data used for analyzing contrast agent arrival, exit, inflow, or outflow may be stored. Transform data for relating coordinate systems may be stored.

For volume data, the stored data representing contrast agents may be interpolated or converted to an evenly spaced three-dimensional grid or remain in a scan format. Each datum is associated with a different volume location (voxel) in the patient volume. Each volume location is the same size and shape within the dataset. Volume locations with different sizes, shapes, or numbers along a dimension may be included in a same dataset. The voxel size and/or distribution may be different for different types of imaging data.

The memory 12 or other memory is a non-transitory computer readable storage medium storing data representing instructions executable by the programmed processor 24 for contrast agent imaging. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for scan timing, the method comprising:
    injecting ultrasound contrast agents into a patient as a test bolus;
    scanning a first region of a patient with ultrasound;
    detecting, from the scanning, the ultrasound contrast agents in the first region;
    determining a length of time from injecting to the detection of the ultrasound contrast agents in the first region; then determining a length of time for magnetic resonance or computed tomography contrast agents to reach the first region or a second region from injection based on the length of time from the injecting to the detection of the ultrasound contrast agents;

injecting magnetic resonance or computed tomography contrast agents into the patient;

scanning the first region or the second region of the patient with a magnetic resonance or computed tomography system; and triggering the scanning with the magnetic resonance or computed tomography system based on the determined length of time for magnetic resonance or computed tomography contrast agents to reach the first region or a second region from injection.

2. The method of claim 1 wherein scanning the first region with ultrasound comprises transmitting acoustic energy to the first region and receiving echoes responsive to the transmitting from the first region.

3. The method of claim 1 wherein detecting comprises detecting a non-linear fundamental response of the contrast agents.

4. The method of claim 1 wherein determining the length of time from injecting to the detection of the ultrasound contrast agents in the first region comprises determining a time from the injecting of the test bolus of the ultrasound contrast agents into the patient to initial detection of the ultrasound contrast agents at the first region.

5. The method of claim 1 wherein determining the length of time from injecting to the detection of the ultrasound contrast agents in the first region comprises determining a time for the ultrasound contrast agents to wash-in to the first region.

6. The method of claim 1 wherein determining the length of time from injecting to the detection of the ultrasound contrast agents in the first region comprises determining a time for the ultrasound contrast agents to wash-out of the first region.

7. The method of claim 1 wherein scanning with the magnetic resonance or computed tomography system comprises imaging the magnetic resonance or computed tomography contrast agents.

8. The method of claim 1 wherein triggering comprises starting or stopping the scanning with the magnetic resonance or computed tomography system.

9. The method of claim 1 wherein determining the length of time from injecting to the detection of the ultrasound contrast agents in the first region comprises determining a time for the ultrasound contrast agents relative to the first region where the first region comprises a sub-region of the second region for the scanning with the magnetic resonance or computed tomography system, and wherein triggering comprises setting a duration of the scanning based on the timing, the duration being for scanning multiple times.

10. The method of claim 1 wherein scanning with ultrasound comprises repetitively acquiring data representing the first region, wherein scanning with the computed tomography system comprises avoiding the scanning and corresponding radiation dose for a period based on the timing and the triggering.

11. The method of claim 1 wherein triggering comprises arranging for the scanning with the magnetic resonance system to capture arrival, wash-in, wash-out or combinations thereof given a scan time of the magnetic resonance system.

12. A system for scan timing, the system comprising:
first contrast agents comprising ultrasound contrast agents;
second contrast agents comprising non-ultrasound contrast agents;
an ultrasound scanner configured to monitor the first contrast agents in a patient;
an imaging system other than the ultrasound scanner, the imaging system configured to monitor the second contrast agents in the patient; and
an interface between the ultrasound scanner and the imaging system, the imaging system configured to time acquisition of data representing the second contrast agents, the timing of the acquisition being a function of data representing the first contrast agents from the ultrasound scanner;
wherein the interface is configured to determine a length of time from infection to the detection of the first contrast agent in a first region, to determine a length of time for the second contrast agents to reach the first region or a second region from injection based on the length of time from the injection to the detection of the first contrast agents; and to trigger scanning with the imaging system based on the determined length of time for the second contrast agents to reach the first region or a second region from injection.

13. The system of claim 12 wherein the interface comprises a processor, the processor configured to determine the time of the acquisition based on an amount of time from injection of the first contrast agents to detection of the first contrast agents in a region of interest.

14. The system of claim 12 wherein the interface comprises a processor, the processor configured to determine the time of acquisition by the imaging system as being when the first contrast agents are detected by the ultrasound scanner or being a period after when the first contrast agents are detected by the ultrasound scanner.

15. The system of claim 12 wherein the interface comprises a processor, the processor configured to determine the time of acquisition as lasting through wash-in or wash-out for different parts of a region of interest.

16. A non-transitory computer readable storage medium having stored therein data representing instructions executable by a programmed processor for contrast agent imaging, the storage medium comprising instructions for:
scanning a first region of a patient with ultrasound;
detecting, from the scanning, ultrasound contrast agents in the first region;
determining a length of time from injecting to the detection of the ultrasound contrast agents in the first region; then
determining a length of time for magnetic resonance or computed tomography contrast agents to reach the first region or a second region from injection based on the length of time from injecting to the detection of the ultrasound contrast agents in the first region;
timing acquisition of a magnetic resonance or computer tomography contrast agent image, the timing based on the determined length of time for the magnetic resonance or computer tomography contrast agents to teach the first region from injection; and
acquiring the contrast agent image in response to the timing.

17. The non-transitory computer readable storage medium of claim 16 wherein acquiring comprises acquiring data representing contrast agents detected with magnetic resonance or computed tomography, the contrast agent image being of the contrast agents detected with magnetic resonance or computed tomography.

18. The non-transitory computer readable storage medium of claim 16 wherein timing comprises determining a duration for the acquiring, the duration being a period of multiple scans.

* * * * *